United States Patent [19]

Kellan

[11] Patent Number: 5,361,780
[45] Date of Patent: Nov. 8, 1994

[54] HEAD STABILIZER AND SUPERIOR RECTUS BRIDLE SUTURE FIXATOR DEVICE AND DRAINAGE DEVICE FOR USE IN EYE SURGERY AND METHODS THEREFOR

[76] Inventor: Robert E. Kellan, 60 East St., Suite 1100, Methuen, Mass. 01844

[21] Appl. No.: 865,531

[22] Filed: Apr. 9, 1992

Related U.S. Application Data

[63] Continuation-in-part of Ser. No. 808,724, Dec. 17, 1991.

[51] Int. Cl.⁵ .................. A61B 19/00; A61B 19/08; A61F 5/37
[52] U.S. Cl. .................. 128/849; 128/853; 128/870; 128/876
[58] Field of Search .................. 128/849–856, 128/845, DIG. 26, 853, 857, 858, 869, 870, 876; 602/17, 14

[56] References Cited

U.S. PATENT DOCUMENTS

| | | |
|---|---|---|
| 2,492,383 | 12/1949 | Jones . |
| 3,086,529 | 4/1963 | Munz et al. . |
| 3,190,444 | 6/1965 | Kelson . |
| 3,315,671 | 4/1967 | Creelman . |
| 3,358,141 | 12/1967 | Hoffmann et al. . |
| 3,469,268 | 9/1969 | Phillips . |
| 3,586,001 | 6/1971 | Sanderson . |
| 3,889,668 | 6/1975 | Ochs et al. . |
| 3,897,777 | 8/1975 | Morrison ................ 128/869 |
| 4,058,112 | 11/1977 | Johnson ................ 128/845 |
| 4,108,170 | 8/1978 | Spann . |
| 4,182,322 | 1/1980 | Miller . |
| 4,299,209 | 11/1981 | Behrens et al. . |
| 4,550,713 | 11/1985 | Hyman . |
| 4,570,628 | 2/1986 | Neal ................ 128/853 |
| 4,665,566 | 5/1987 | Garrow ................ 2/171 |
| 4,700,691 | 10/1987 | Taci et al. . |
| 4,707,031 | 11/1987 | Meistrell . |
| 5,015,251 | 5/1991 | Cherubini . |
| 5,020,533 | 6/1991 | Hubbard ................ 128/857 |
| 5,027,833 | 7/1991 | Calkin . |
| 5,038,798 | 8/1991 | Dowdy ................ 128/853 |
| 5,042,507 | 8/1991 | Dowdy ................ 128/849 |
| 5,081,665 | 1/1992 | Kostich ................ 378/208 |

FOREIGN PATENT DOCUMENTS

| | | |
|---|---|---|
| 725072 | 3/1955 | United Kingdom . |
| 8101513 | 6/1981 | WIPO . |

Primary Examiner—Michael A. Brown

[57] ABSTRACT

A surgical drape and head stabilizer device includes a surgical drape and a strap made or assembled as part of the surgical drape to be secured laterally around the head of a patient lying in a supine position on an operating table and around the operating table to hold the patient's head in a stabilized, non-moving position during eye surgery. The drape or strap carries a fixation surface to be disposed along the patient's forehead for fixating a superior rectus bridle suture with controlled tension to optimally position the eye for surgery while allowing the tension and fixation site for the superior rectus bridle suture to be adjusted during surgery to reposition the eye. A surgical drape and drainage device includes a surgical drape, a fluid collection bag on the surgical drape, a drain for communicating with the eye and the fluid collection bag to drain excess fluid from the eye into the fluid collection bag and a drain holder on the drape for releasably securing the drain.

32 Claims, 2 Drawing Sheets

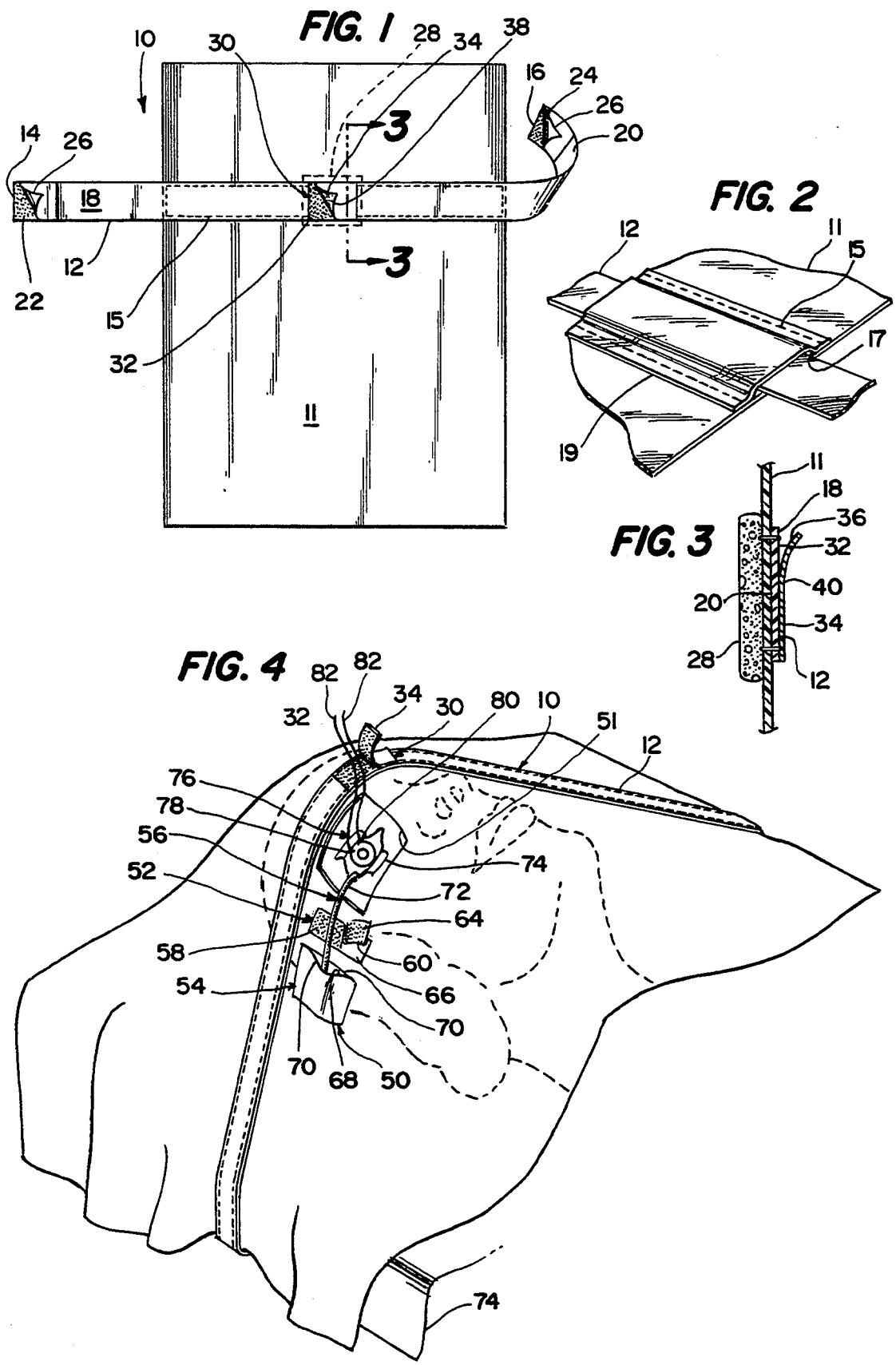

HEAD STABILIZER AND SUPERIOR RECTUS BRIDLE SUTURE FIXATOR DEVICE AND DRAINAGE DEVICE FOR USE IN EYE SURGERY AND METHODS THEREFOR

CROSS REFERENCE TO RELATED APPLICATION

This application is a continuation-in-part of U.S. patent application Ser. No. 07/808,724 filed Dec. 17, 1991.

BACKGROUND OF THE INVENTION

1. Field of the Invention

The present invention relates to eye surgery and, more particularly, to head stabilizers, superior rectus bridle suture fixators and drainage devices particularly useful in cataract surgery and to methods of performing eye surgery while stabilizing a patient's head, fixating superior rectus bridle sutures and securing a drain to drain fluids from the eye.

2. Discussion of the Prior Art

During eye surgery, a patient typically lies on an operating table with the back of the patient's head supported on a head support part of or associated with the operating table. A surgeon is usually positioned adjacent the head support to approach the patient's eye from the top of the patient's head and over the frontal bone, or forehead, of the patient. The head support prevents some movement of the patient's head during surgery; however, the patient's head can still move during surgery due to forces applied by the surgeon or due to movement by the patient since the patient is usually anesthetized locally and, therefore, capable of voluntary head motion. Movement of the patient's head is undesirable during eye surgery and, in particular, cataract surgery, and can lead to substantial complications. During cataract surgery, various surgical instruments are inserted in the eye including instruments for forming an incision in the conjunctiva and limbus, for performing a capsulotomy, for removing the cataractous natural lens, for irrigating and aspirating, and for inserting a lens implant. Accordingly, the patient's head must be held stable to allow precise positioning of the surgical instruments and to avoid damage to surrounding tissue and eye structure from inadvertent contact with the instruments caused by unexpected head movements. Even slight movements of the patient's head during cataract surgery can increase the difficulty of the surgical procedure and can produce adverse consequences due to the precision of the procedure and the small space in which the surgeon has to operate. When the phacoemulsification technique for lens removal is employed, lens tissue is fragmented with an instrument having an ultra-sound tip moving at very high speeds, i.e. approximately 40,000 times per second, while fragmented tissue is aspirated through the instrument. Movement of the patient's head can impair accurate placement of the phacoemulsifier probe resulting in destruction of and/or aspiration of healthy eye tissue. Furthermore, it may be desirable in certain instances for the patient's head to be tilted laterally to one side or the other during surgery to optimize exposure of the eye; however, such head positions are usually precluded during cataract surgery due to the inability to maintain the patient's head at the desired angle for the duration of the surgical procedure, particularly when the patient is anesthetized locally. Head stabilizers for use in eye or cataract surgery have been proposed in applicant's co-pending patent application referenced hereinabove to stabilize and prevent movement of a patient's head during eye surgery. Because it is advantageous to minimize the duration and complexity of surgical procedures of the eye, it is desirable for the head stabilizers to be positioned on a patient simultaneously with surgical drapes used to cover a patient's head and face during eye surgery such that multiple steps of the procedures can be consolidated and thusly simplified.

There is a great need for head restraints and, in particular, head restraints incorporated into surgical drapery, for many other eye procedures performed under local anesthesia such as, for example, photorefractive keratectomy wherein a laser is used to modify corneal curvature to eliminate refractive errors such that any movement of the head during the procedure may comprise the results.

It is also important during eye surgery to immobilize the eye itself; and, accordingly, a bridle suture is usually employed for holding the superior rectus muscle of the eye to restrain and optimally position the eye for surgery. The superior rectus bridle suture is conventionally formed by inserting a needle with a length of suture material attached thereto through the conjunctiva at an entry point located 8 to 10 mm behind the limbus and adjacent a lateral side of the superior rectus, grasping the superior rectus with a muscle forceps, lifting the superior rectus outwardly from the eye, inserting the needle under the raised superior rectus and pulling the needle and suture material through the conjunctiva to exit the eye at a point disposed adjacent an opposing lateral side of the superior rectus. The suture material thusly extends under the superior rectus transversely, or laterally, with ends of the suture material extending from the entry and exit points externally of the eye. The ends of the suture material are grasped and pulled with desired tension in the direction of the patient's forehead such that the superior rectus is lifted by the bridle suture to optimally position the eye in the optic orbit. The superior rectus and, therefore, the eye, is conventionally held in a desired position by securing the ends of the suture material with clamps or tape to the surgical drape covering the patient's head and face or by securing the ends of the suture material to a clamp that is positioned to allow the weight of the clamp to provide tension. Conventional methods for securing the superior rectus bridle suture possess numerous disadvantages including the inability to control the position of the eye, failure to maintain uniform tension on the superior rectus during the surgical procedure, difficulty in changing the position of the eye during the surgical procedure, possible obstruction of the surgical field and decreased reliability due to the increased opportunity for the ends of the suture material to move or become disengaged from the securement site. Bridle suture fixator devices have been proposed in applicant's co-pending patent application referenced hereinabove to allow superior rectus bridle sutures to be fixated with controlled tension along head stabilizers mounting the bridle suture fixator devices. It is desirable for the bridle suture fixator devices to be incorporated into surgical drapery, with or without the head stabilizers, such that the bridle suture fixator devices can be positioned on a patient simultaneously with a surgical drape thusly minimizing the number of steps required in surgical procedures of the eye.

Another very important consideration in eye surgery is to drain fluid that accumulates in the eye during surgery. Excess fluid that accumulates or pools in the eye, either from natural tearing or as the result of saline or other irrigating fluids supplied to the eye during surgery, must be removed from the eye because such fluid can impair the surgical procedure. Where surgical procedures of the eye are conducted with microscopic visualization, excess fluid in the eye can diminish a surgeon's depth of field under the microscope; and, in cataract surgery, excess fluid can obstruct a surgeon's visibility during intraocular lens maneuvers. Excess fluid is commonly removed from the eye during eye surgery by "mopping up" the fluid using small, absorbent spears or by draining the fluid from the eye using a drain communicating with the eye. Where spears are employed, the circulating nurse must continually apply the spears to the eye such that the hands and attention of the nurse are diverted from other tasks and the spears can obstruct the surgeon's view of the eye. The spears also increase the cost of surgical procedures of the eye in that the number of spears used in a single surgical procedure can be considerable. Where drains are used to remove fluid from the eye, there is no way to effectively secure and position the drains and, in particular, to attach or secure the drains to surgical drapery, and the drains cannot be easily replaced and repositioned during eye surgery.

SUMMARY OF THE INVENTION

Accordingly, it is a primary object of the present invention to overcome the aforementioned disadvantages of the prior art by allowing a surgeon to position a patient's head for optimal exposure during eye surgery and keep the head from moving during the surgical procedure with a head stabilizer capable of being positioned on the patient's head simultaneously with placement of a surgical drape.

Another object of the present invention is to facilitate eye surgery by stabilizing a patient's head to prevent lateral and forward movements.

It is also an object of the present invention to provide a head stabilizer made or assembled as part of a surgical drape allowing the head stabilizer to be positioned with the surgical drape upon a patient's head.

A further object of the present invention is to provide a method of performing eye surgery including positioning a bridle suture fixator device on a patient's head simultaneously with a surgical drape and fixating a superior rectus bridle suture on the bridle suture fixator with controlled, uniform tension and while allowing the tension and fixation site for the superior rectus bridle suture to be easily adjusted during surgery to reposition the patient's eye.

An additional object of the present invention is to provide a superior rectus bridle suture fixator made or assembled as part of a surgical drape allowing the bridle suture fixator to be positioned, via the surgical drape, along the forehead of a patient undergoing eye surgery for fixating a superior rectus bridle suture securely thereon without the need for clamps, tape or other extraneous securing devices.

Yet another object of the present invention is to provide a bridle suture fixator on a head stabilizer made or assembled as part of a surgical drape allowing both the head stabilizer and bridle suture fixator to be positioned on a patient's head simultaneously with placement of the surgical drape.

The present invention has another object in providing a system for performing eye surgery including an operating table for supporting a patient in a supine position, a surgical drape for covering the patient's head with an opening exposing an eye to be operated, and a head stabilizer secured to the surgical drape for holding the patient's head in a stabilized non-moving position, the head stabilizer extending across the forehead of the patient and around the operating table and having opposing ends carrying fasteners for securing the opposing ends together to hold the head of the patient against the operating table.

Furthermore, it is an object of the present invention to provide a drainage device on a surgical drape for covering a patient's head with an opening in the drape exposing an eye of the patient to be operated such that a drain communicating with the eye can be selectively positioned and secured on the drainage device.

The present invention has as a further object to provide a drainage device made or assembled as part of a surgical drape allowing the drainage device to be positioned with the surgical drape over a patient's head with an opening in the drape exposing an eye of the patient to be operated whereby a drain communicating with the eye can be selectively fixated on the drainage device.

Another object of the present invention is to provide a method of performing eye surgery including selectively positioning a drainage wick communicating with an eye on a drain holder and releasably securing the drainage wick on the drain holder permitting the drainage wick to be immovably held during eye surgery while allowing the drainage wick to be repositioned and replaced during eye surgery.

Yet a further object of the present invention is to provide a drainage device including a drain holder and a fluid collection bag secured on a surgical drape for covering a patient's head during eye surgery with an opening in the drape exposing an eye of the patient to be operated and a drain removably securable on the drain holder in communication with the eye and the collection bag.

Some of the advantages of the present invention are that surgical instruments can be positioned in the eye during cataract surgery with enhanced precision and safety, damage to healthy eye tissue and structures due to inadvertent head movement is minimized, superior rectus bridle sutures can be fixated during eye surgery with precision and reliability and without obstruction of the surgical field, a patient's head can be stabilized during cataract surgery in a simple and comfortable manner, multiple steps of surgical procedures of the eye can be consolidated in a single step, surgical procedures of the eye are simplified, the duration of eye surgery can be reduced, eye surgery can be conducted utilizing a fewer number of separate medical products, product inventories for surgical procedures of the eye can be simplified, the costs associated with eye surgery can be reduced, visualization of the eye during eye surgery is enhanced, intraocular lens maneuvers are promoted, duties of circulating nurses are facilitated, the superior rectus bridle suture fixator, head stabilizer and drainage devices are compatible for use with diverse sizes and types of operating tables or head supports and diverse sizes and types of surgical drapery and can be economically disposable for single patient use.

The present invention is generally characterized in a head stabilizer and superior rectus bridle suture fixator including a strap made or assembled as part of a surgical drape for covering a patient's head and face during eye surgery, the strap being positioned simultaneously with placement of the drape to extend over the patient's forehead laterally encircling the patient's head and an operating table supporting the patient's head for surgery. The strap includes opposing ends having fasteners thereon allowing the ends to be releasably secured together in overlapping engagement to maintain the strap in a position tightly encircling the patient's head and the operating table. The superior rectus bridle suture fixator includes an adhesive fixation surface disposed on the strap or on a proximal surface of the drape to be positioned, via placement of the drape, along the patient's forehead and a cover removably secured on the fixation surface for selectively exposing at least a portion of the fixation surface to allow a superior rectus bridle suture formed in the patient's eye to be fixated on the fixation surface with controlled, uniform tension to position the eye for surgery and to permit the tension and/or fixation site for the bridle suture to be adjusted during surgery to reposition the eye. A drainage device according to the present invention includes a drain holder and a fluid collection bag attached to a surgical drape and a drain for being removably, selectively secured on the drain holder in communication with an eye of the patient and the fluid collection bag. The drain holder and fluid collection bag are positioned on the surgical drape to be disposed along a part of the drape that is at a lower elevation than the patient's eye when the drape is placed over the patient's head such that fluid flows by gravity via the drain into the fluid collection bag.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a reduced, top plan view of a surgical drape having a head stabilizer and superior rectus bridle suture fixator device according to the present invention.

FIG. 2 is a broken perspective view of a modification of a surgical drape having a head stabilizer according to the present invention.

FIG. 3 is a broken sectional view taken along line 3—3 of FIG. 1.

FIG. 4 is a perspective view of a further modification of a surgical drape having a head stabilizer and a superior rectus bridle suture fixator device and drainage device according to the present invention, the drape being shown in use covering the head of a patient.

DESCRIPTION OF THE PREFERRED EMBODIMENTS

Figure 5:
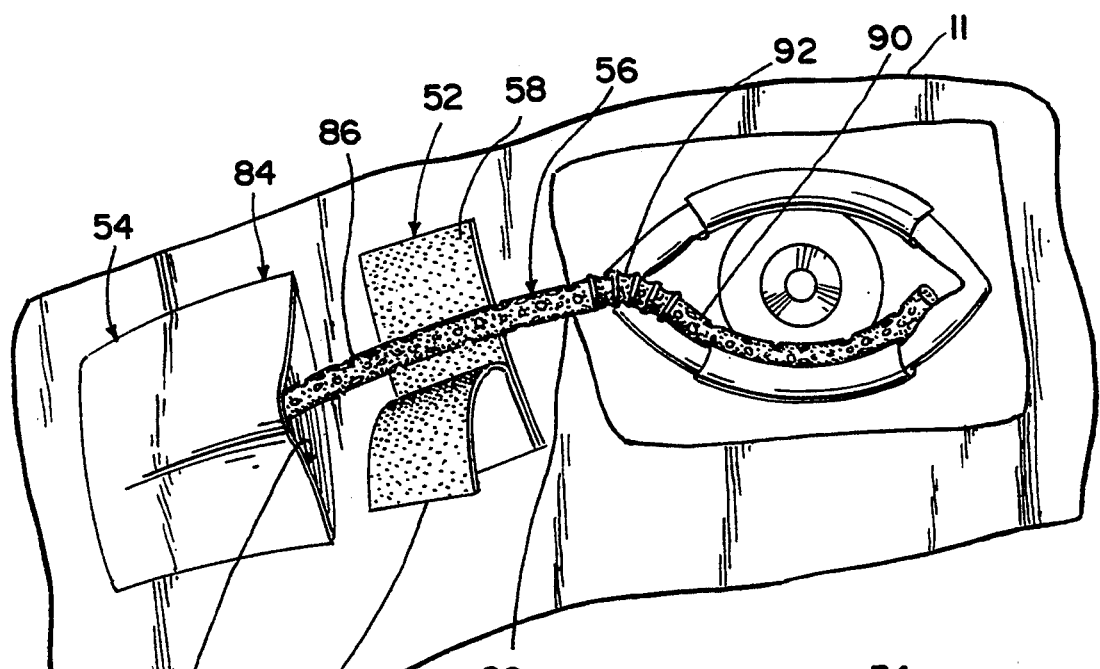
FIG. 5 is an enlarged, broken top view of a modification of a drainage device according to the present invention on a surgical drape, the drape being shown in use covering the head of a patent.

A head stabilizer and superior rectus bridle suture fixator device according to the present invention is shown at 10 in FIG. 1, the superior rectus bridle suture fixator device 10 being incorporated in a surgical drape 11. The surgical drape 11 is conventional in configuration and construction and can be made of any suitable sterile material, including paper, cloth, plastic and vinyl, to provide a sterile field in the vicinity of an eye of a patient to be operated. The drape 11 can have various sizes and configurations, including rectangular and square as well as other configurations; and, preferably, the drape 11 is rectangular in configuration measuring approximately 70 inches×61 inches to cover the head and upper body of a patient lying upon an operating table with the back of the patient's head supported on the operating table such that the drape extends over and along top and opposing lateral sides of the operating table. It will be appreciated that the drape 11 can be made as a single layer or as multiple layers depending upon the material and manner of construction for the drape and that the drape can be provided with an appropriately sized and located opening to be placed over the patient's eye to expose the eye for surgery. The head stabilizer and superior rectus bridle suture fixator device 10 includes a strap, or strip, belt or band, 12 of material secured or attached to the drape 11 and extending lengthwise with a substantially uniform width between opposing free ends 14 and 16. The strap 12 is secured on the drape 11 at a location allowing the strap 12 to be positioned over the frontal bone, or forehead, of the patient with the ends 14 and 16 extending downwardly along the opposing lateral sides of the operating table. Where the drape 11 is rectangular having a pair of long, or lateral, sides, and a pair of short, or top and bottom sides, as shown in FIG. 1, it is preferred that the strap extend lengthwise along the width of the drape 11 such that the strap is disposed substantially parallel to the short sides of the drape with the strap terminating at ends 14 and 16 beyond the long sides. The length of the strap 12 measured between the ends 14 and 16 is selected to allow the ends 14 and 16 to be positioned in overlapping arrangement beneath the operating table with the strap tightly encircling the patient's head and the operating table laterally. It is preferred that the strap 12 be disposed closer to one of the short sides and, in particular, the top side, of the drape 11 than the other, or bottom side, to form a relatively longer extension of the drape 11 between the strap 12 and the bottom side allowing the longer extension to extend over and cover the upper body and torso of the patient with the strap 12 positioned over the patient's forehead. A relatively shorter extension of the drape 11 is defined between the strap 12 and the top side, the shorter extension being of a size sufficient to extend over and cover the top of the patient's head and, preferably, the top side of the operating table. The strap 12 can be made of many various, sterile materials including cloth, plastic, vinyl and paper and can be secured to the drape 11 in many various ways depending upon the materials and construction for the drape 11 and the strap 12. As one example, the strap 12 can be secured on a forward facing or proximal surface of the drape 11 by being sewn or stitched onto the proximal surface of the drape as shown at 15 in FIG. 1. It will be appreciated that the strap 12 can be secured on drape 11 in many other ways such as by adhesives, heat sealing and bonding techniques, the strap being mounted in a sleeve or pocket of the drape, the strap being formed as a layer of the drape where the drape includes multiple layers and the drape itself being reinforced such that a section of the drape functions as a strap or band. The strap 12 can be secured on the drape 11 at various locations including the proximal surface of the drape, a rearward or distal surface of the drape or within the material or layers of the drape. As shown in FIGS. 1 and 3, an upper or proximal surface 18 of the strap 12 is separated from a lower or distal surface 20 thereof by a minimal thickness substantially uniform along the length of the strap. A layer 22 of activated adhesive is provided as a fastener on the upper surface 18 adjacent the end 14, and a layer 24 of activated adhesive is provided as a fastener on the lower surface 20 adjacent the end 16 for adhesively engaging the layer 22. Protective release sheets 26 are disposed over and completely cover the adhesive layers 22 and 24, respectively, with the release sheets 26 being removably secured on the layers 22 and 24. The release sheets 26 can be manually peeled away from the strap 12 with a force sufficient to overcome the bond between the release sheets and the adhesive layers 22 and 24, respectively, to selectively expose the adhesive layers 22 and 24. A cushion, or pad, 28 can be secured on a distal surface of the drape 11 or on the lower surface 20 of the strap 12 to be positioned centrally between the ends 14 and 16 and, therefore, the lateral sides of the drape 11 for positioning over the frontal bone, or forehead, of the patient upon the operating table. Removal of the release sheets 26 to reveal the adhesive layers 22 and 24 allows the ends 14 and 16 to be adhesively secured together, by placing the adhesive layers 22 and 24 in overlapping contact, beneath the operating table to hold the strap 12 taut and to be released when the ends 14 and 16 are pulled apart with a force sufficient to overcome the adhesive bond between the layers 22 and 24. The length of the adhesive areas on either or both of the ends 14 and 16 is preferably large enough to permit the overlap of the ends 14 and 16 to vary to ensure that the drape 11 with the head stabilizer can be used with various sizes and types of operating tables, and the release sheets 26 can be unitary or made of multiple parts. Similarly, the adhesive layers 22 and 24 need not overlap in use in that layer 22 can be made to adhere to any portion of surface 20 while layer 24 can be made to adhere to any portion of surface 18. It will be appreciated that the length of the strap 12 can vary and that the ends 14 and 16 can terminate at the long or lateral sides of the drape 11 permitting the length of the strap to be the same as the width of the drape. Where the ends 14 and 16 do not protrude beyond the long sides of the drape 11, one or both of the surfaces 18 and 20 can be surfaces of the drape in accordance with the manner in which the strap is secured to the drape; and accordingly, where the strap 12 is secured on the proximal surface of the drape 11, the upper surface 18 is defined on the strap 12 while the lower surface 20 is defined by the distal surface of the drape and, where the strap is formed as an inner layer of the drape, the surfaces 18 and 20 will be defined, respectively, by the proximal and distal surfaces of the drape.

FIG. 2 shows a sleeve or pocket 17 formed on the proximal surface of drape 11 with the strap 12 being mounted in the sleeve or pocket 17. The sleeve or pocket 17 can be formed in many various ways; and, as shown in FIG. 2, the sleeve or pocket 17 is formed by securing a strip 19 of material to the drape 11 such as by stitching or sewing at 15. It will be appreciated that the sleeve or pocket 17 can be formed on either the proximal or distal surfaces of the drape 11 or within layers of the drape where the drape is made of multiple layers or ply.

As shown in FIGS. 1 and 3, a superior rectus bridle suture fixator 30 is provided on the head stabilizer and includes a fixation surface or layer 32 of activated adhesive disposed on the upper surface 18 centrally between the ends 14 and 16 and, therefore, the long sides of the drape 11, and a cover sheet 34 disposed over the fixation surface 32. A lower face 36 of the cover sheet 34 is at least coextensive in area with the fixation surface 32 to completely cover the fixation surface, and a layer 38 of activated adhesive is provided on the lower face 36 for being releasably, adhesively secured to the fixation surface 32. An upper or forward face 40 of the cover sheet 34 has a non-adhesive surface. The cover sheet 34 can be manually grasped and peeled away from the strap 12 with a force sufficient to overcome the adhesive bond between the fixation surface 32 and the adhesive layer 38 to reveal all or a selected part of the fixation surface 32 for fixation of superior rectus bridle sutures thereon. The cover sheet 34, once removed in whole or in part from the strap 12, can be re-secured on the strap by pressing the adhesive layer 38 against the fixation surface 32.

Preferably, the strap 12 is made of a thin, sterile, paper or cloth fabric or the like, with one preferred material being Dermicel Hypoallergenic Tape manufactured by Johnson & Johnson. The cushion 28 is preferably made from a sterile, soft material, such as gauze and the like, capable of cushioning and protecting a patient's forehead when the strap 12 is tightened around the patient's head and the operating table, and the cushion is preferably sized to cover a substantial portion of a patient's forehead laterally. The length of the strap 12 is selected to allow the strap to be used with various width operating tables to encircle a patient's head and the operating table laterally while permitting a generous overlap of the ends 14 and 16 beneath the operating table, such that the ends 14 and 16 can be overlapped a greater or lesser extent to accommodate operating tables of diverse widths. The adhesive layers 22 and 24 are sufficiently large in surface area to ensure secure attachment of the ends 14 and 16 and to permit adjustment of the overlap for different sizes of operating tables while maintaining the integrity of the attachment at the ends. The fixation surface 32 is preferably large enough in surface area to offer a range of fixation sites for superior rectus bridle sutures in either of a patient's eyes and to ensure secure fixation of bridle sutures thereon. The fixation surface 32 can be provided on the upper surface 18 of the strap 12 as well as on the proximal surface of drape 11 where the strap 12 is not disposed on the proximal surface but, rather, within or on the distal surface of the drape. According to a preferred embodiment, the strap 12 has an overall length of approximately 65 inches and a width of approximately 3 inches; the adhesive layers 22 and 24 extend transversely the full width of the strap, i.e. approximately 3 inches, and lengthwise along the strap from the ends 14 and 16, respectively, approximately 20 inches; the cushion 28 extends transversely the full width of the strap and lengthwise along the strap approximately 10 inches; the fixation surface 32 extends transversely the full width of the strap and lengthwise along the strap approximately 10 inches; and the drape 11 with the head stabilizer and superior rectus bridle suture fixator device attached thereto is sterile and disposable for single patient use.

It will be appreciated that the ends 14 and 16 can be secured together in various ways in addition to the adhesive layers 22 and 24; and, as one example, the adhesive layers 22 and 24 can be replaced with strips of cooperative, interlockingly engagable material, including complementary hook and loop type interlocking material such as Velcro ®, as fasteners on the ends 14 and 16. It will also be appreciated that the strap 12 can have lengths greater or less than the width of the drape 11 and that the strap need not be secured to the drape continuously along the width of the drape. The pad 28 can be eliminated from strap 12, if desired, such that the drape 11 with the head stabilizer and bridle suture fixator device 10 can be provided with or without the pad 28. Where the pad 28 is provided, the pad can be disposed between the strap 12 and the drape 11, within material or layers of the drape as well as along the distal surface of the drape 20. For surgical procedures not requiring fixation of bridle sutures, the drape 11 can be provided with a head stabilizer alone without the bridle suture fixator 30.

A drainage device according to the present invention is shown at 50 in FIG. 4 and includes a drain holder 52 and a fluid collection bag 54 secured on drape 11 and a drain 56. The drain holder 52 includes an attachment surface or layer 58 of activated adhesive secured on the proximal surface of the drape 11 and a cover sheet 60 disposed over the attachment surface 58. The drain holder 52 is located on the drape 11 closer to one of the lateral sides of the drape than the other such that the drain holder 52 is disposed laterally between the one lateral side and an eye of the patient to be operated with the drape covering the patient's head and face to position the drain holder along a part of the drape that extends downwardly, laterally from the patient's face. The attachment surface 58 can be formed as a layer or coating of activated adhesive directly applied on the material of the drape 11 or as a separate sheet secured on the drape 11 in various ways including sewing or stitching and adhesive and other forms of bonding. A lower face of the cover sheet 60 is at least coextensive in area with the attachment surface 58 to completely cover the attachment surface, and a layer 64 of activated adhesive is provided on the lower face for being releasably, adhesively secured to the attachment surface 58. An upper or forward face 66 of the cover sheet 60 has a non-adhesive surface. The cover sheet 60, can be manually grasped and peeled away from the attachment surface 58 with a force sufficient to overcome the adhesive bond between the attachment surface 58 and the adhesive layer 64 to reveal all or a selected part of the attachment surface for fixation of the drain 56 thereon. The cover sheet 60 once removed in whole or in part from the attachment surface 58, can be re-secured on the attachment surface by pressing the adhesive layer 64 against the attachment surface 58. The fluid collection bag 54 is preferably made of a fluid impervious material, such as plastic, and has a closed lower end and a selectively closable upper end 68 disposed adjacent the drain holder 52 and laterally aligned with the drain holder between the drain holder and the one lateral side of the drape 11. The upper end 68 has a pair of opposing upper edges 70, and opposing inner surfaces of the fluid collection bag 54 having layers of activated adhesive thereon along the edges 70 allowing the upper end 68 of the fluid collection bag 54 to be selectively closed by pressing the edges 70 together and to be selectively opened by pulling apart the edges 70. It will be appreciated that the upper end 68 of the fluid collection bag 54 can be selectively closed and opened in various other ways and that the structure and/or material of construction for the bag itself can be utilized to make the upper end self-sealing, such as by forming a forward facing or proximal upper edge of the bag to be resilient and deformable to selectively open and close the bag upon manipulation of the proximal upper edge. The fluid collection bag 54 can be secured to the proximal surface of the drape 11 by any suitable means, such as adhesives. The drain 56 includes an elongate wick 72 of absorbent material having a cylindrical body terminating at ends designed to communicate, respectively, with the eye to be operated and the fluid collection bag 54. The wick 72 can be made from various absorbent material, such as various fabrics, fibers and sponges, capable of absorbing excess fluid from the eye via contact of the wick with the fluid at the eye. The length of the wick 72 between the ends is selected to allow an end of the wick to be disposed at an outer corner or outer can thus of the eye with the other end of the wick disposed within the upper end 68 of the fluid collection bag 54. The wick 72 can have various configurations including straight, curved and bent configurations in accordance with the locations of the fluid collection bag 54, the drain holder 50 and the part of the eye to be contacted by the wick. The drainage device 50 can be provided on drape 11 at various centrally offset locations to be compatible with right or left eye surgical procedures; however, various other locations for the drainage device 50 on the drape 11 can be selected in accordance with desired positions for the wick 72 for diverse surgical procedures in that the wick can be positioned at various locations along the eye and not just at an outer corner thereof. The drainage device 50 can thusly be positioned on the drape 11 to allow ends of the wick 72 to communicate with both the eye and the fluid collection bag 54 while being held by the drain holder 52 with the fluid collection bag at a lower elevation than the end of the wick communicating with the eye.

According to a method of operation for the present invention in eye surgery as shown in FIG. 4, the drape 11 is placed or draped, with the proximal surface of the drape facing the surgeon, over the head and upper body of a patient lying in a supine position on an operating table 48 with the back of the patient's head supported on the operating table or a head support part of or associated with the operating table while simultaneously positioning the strap 12 over the frontal bone, or forehead, of the patient. Where a pre-cut opening is provided in the drape 11 to expose an eye to be operated, the opening is positioned over the patient's eye to be operated. Where the pad 28 is provided, the pad is positioned upon the patient's forehead simultaneously with placement of the drape 11 such that the pad extends laterally along the patient's forehead. Where a pad 28 is not provided, the strap 12 is centered on the patient's forehead simultaneously with placement of the drape such that the patient's forehead is disposed centrally between the ends 14 and 16. Where the bridle suture fixator 30 is provided with or without pad 28, the bridle suture fixator is positioned centrally upon the patient's forehead simultaneously with positioning of the drape 11. The drape 11 is arranged such that the strap 12 extends along the patient's forehead and downwardly from the patient's forehead over lateral sides of the patient's head and the operating table as shown in FIG. 4. When utilizing the head stabilizer, the release sheets 26 are manually grasped and pulled away from the strap 12 with force sufficient to overcome the bond between the sheets 26 and the adhesive layers 22 and 24, respectively. The patient's head is properly positioned on the operating table 48 to optimize exposure of the eye undergoing surgery, and the ends 14 and 16 of the strap are positioned in overlapping arrangement beneath the operating table 48. The ends 14 and 16 are pulled to tighten the strap around the patient's head and the operating table laterally and, with the strap held taut, the adhesive layers 22 and 24 are placed in overlapping contact adjacent a lower surface of the operating table 48 to secure the strap in a position tightly encircling the patient's head and the operating table.

Once the patient's head has been satisfactorily stabilized, an opening 51 is made or cut in the drape 11 where a pre-cut opening is not provided to expose the patient's eye to be operated. Where a pre-formed opening is provided in the drape 11, such opening is positioned over the eye to be operated with placement of the drape. With the patient under a local anesthetic, a surgeon approaches the eye from the top of the patient's head and over the patient's forehead, with the eyelids held apart by a clip 74 as shown in FIG. 4. Utilizing a surgical needle having a length of suture material attached thereto, a bridle suture 76 is formed in the patient's eye. In forming the bridle suture 76, the needle is inserted through the conjunctiva at an entry point 78 located approximately 8 to 10 mm behind the limbus and laterally of the superior rectus, the superior rectus is grasped with a muscle forceps and lifted outwardly from the eye, the needle is inserted under the raised superior rectus, and the needle and suture material are pulled through the conjunctiva to exit the eye at an exit point 80 disposed laterally of the superior rectus such that the suture material extends under the superior rectus laterally, or transversely. Free ends 82 of the suture material that extend from the entry and exits points exteriorly of the eye are grasped and pulled with desired tension in the direction of the patient's forehead to hold the superior rectus and optimally position the eye for surgery. In utilizing the bridle suture fixator 30, the cover sheet 34 is manually grasped and peeled away from the fixation surface 32 to expose at least a portion of the fixation surface 32. Depending on whether the sutured eye is the right or left eye of the patient, a right or left side of the cover sheet 34 is peeled away to expose a portion of the fixation surface 32 closest to the sutured eye. With the eye optimally positioned and the desired tension maintained on the ends 82, the ends 82 are positioned over the fixation surface 32 and are pressed thereagainst to be secured thereon by virtue of the adhesive bonding characteristics of the fixation surface. The ends 82 extend across the width of the fixation surface 32 providing continuous fixation therealong. The cover sheet 34 can be folded back over the fixation surface 32 to cover the ends 82 fixated thereon, and the adhesive layer 38 on the cover sheet adheres to the fixation surface 32 and the ends 82. If the eye is not satisfactorily positioned, the cover sheet 34 can be lifted and the ends 82 grasped and pulled away from the fixation surface 32. Once released from the fixation surface 32, the ends 82 can be manipulated to produce a different tension and/or angle to establish a more favorable position for the eye, and the ends 82 can be resecured on the fixation surface 32 to maintain the adjusted position for the eye. With both the head and the eye stabilized, eye surgery and, in particular, cataract surgery, can be performed by the surgeon using standard techniques to introduce instruments into the eye to remove the cataractous natural lens. If, during the course of surgery, eye position needs to be altered, the tension and/or fixation site for the superior rectus bridle suture 76 can be changed to optimize the position of the eye.

According to a method of operation for the drainage device 50, the cover sheet 60 of the drain holder 52 is manually grasped and peeled away from the attachment surface 58 to expose at least a portion of the attachment surface. An end of the wick 72 is positioned at an outer corner or outer can thus of the eye, as shown in FIG. 4, and the other end of the wick is positioned in the upper end 68 of the fluid collection bag 52 with the wick extending across and over the exposed portion of the attachment surface 58. The wick 72 is pressed against the attachment surface 58 and is secured or held thereon due to the adhesive bond of the attachment surface. With the wick 72 secured on the drain holder 52, the wick 72 extends across the width of the attachment surface 58 providing continuous attachment therealong. The cover sheet 60 can be folded back over the attachment surface 58 to cover the wick 72 and, with gentle pressure on the cover sheet 60, the adhesive layer 64 of the cover sheet will adhere to the attachment surface 58 and the wick 72 to secure the wick in position without obstructing the flow of fluid through the wick. The edges 70 of the fluid collection bag 54 can be gently pressed together such that the layers of adhesive along the edges serve to hold the edges together with the wick 72 therebetween to close the upper end 68 of the fluid collection bag without obstructing the flow of fluid through the wick. Excess fluid accumulating in the eye during surgery is absorbed by the wick 72 via the end of the wick communicating with the eye such that the fluid is removed from the eye. Once the wick 72 becomes saturated with absorbed fluid, the fluid drips or flows into the fluid collection bag 54 by gravity via the end of the wick communicating with the fluid collection bag due to the fluid collection bag and the corresponding end of the wick being at a lower elevation than the end of the wick at the eye. Where it becomes necessary to reposition or replace the wick 72, the cover sheet 60 can be grasped and manually peeled away from the attachment surface 58 allowing the wick 72 to be grasped and pulled or lifted away from the attachment surface to release the wick from the drain holder 52. The wick 72 can then be repositioned at the eye or a new wick placed at the eye with the wick being secured on the drain holder 52 to hold the wick in position communicating with the eye and the fluid collection bag 54.

A modification of a drainage device according to the present invention is shown at 84 in FIG. 5 and includes a drain holder 52 and a fluid collection bag 54 secured on drape 11 and a drain 56. The drainage device 84 is substantially the same as the drainage device 50 except for the drain 56. The drain 56 for drainage device 84 includes a wick 86 made of absorbent material and having an elongate, substantially cylindrical segment 88 with an end to be disposed in the upper end 68 of the fluid collection bag 54 and a curved segment 90 joined to the cylindrical segment 88 at a junction 92. The curved segment 90 is configured in accordance with the anatomical curvature of the eye to fit into the inferior fornix of the eye as shown in FIG. 5. The junction 92 is preferably formed as a hinge allowing the cylindrical segment 88 to be bent relative to the curved segment 90 such that the wick 86 can easily bend over the outer canthus of the eye with the curved segment 90 in the inferior fornix. The wick 86 can be made from various absorbent materials, such as various fabrics, fibers and sponges, and can be made in many ways, such as by molding. The junction or hinge 92 can have various structure and arrangements including accordion-like pleats or folds as shown in FIG. 5, a crimp formed in the material of the wick and areas of resilience or relative weakness formed in the wick to permit the wick to bend or deform along the junction 92.

In utilizing the drainage device 84 in cataract surgery, the cover sheet 60 of the drain holder 52 is manually grasped and peeled away from the attachment surface 58 to expose at least a portion of the attachment surface, and the curved segment 90 of the wick 86 is fit into the inferior fornix of the eye. With the curved segment 90 in the inferior fornix, the cylindrical segment 88 is bent, via the junction 92, from the curved segment 90 and over the outer canthus of the eye. The cylindrical segment 88 is positioned over the attachment surface 58 and the end of the cylindrical segment is placed within the upper end 68 of the fluid collection bag 54. With the drain 56 properly positioned in communication with the eye and the fluid collection bag 54, the cylindrical segment 88 is pressed against the attachment surface 58 to adhere to the attachment surface via the adhesive layer of the attachment surface. The cover sheet 60 is then folded back over the attachment surface 58 and, with gentle pressure, is pressed against the attachment surface 58 and the wick 84 to secure the drain 56 in position. It will be appreciated that, depending upon the surgical procedure being performed on the eye, the curved segment 90 can be positioned in the superior fornix of the eye.

Figure 6:
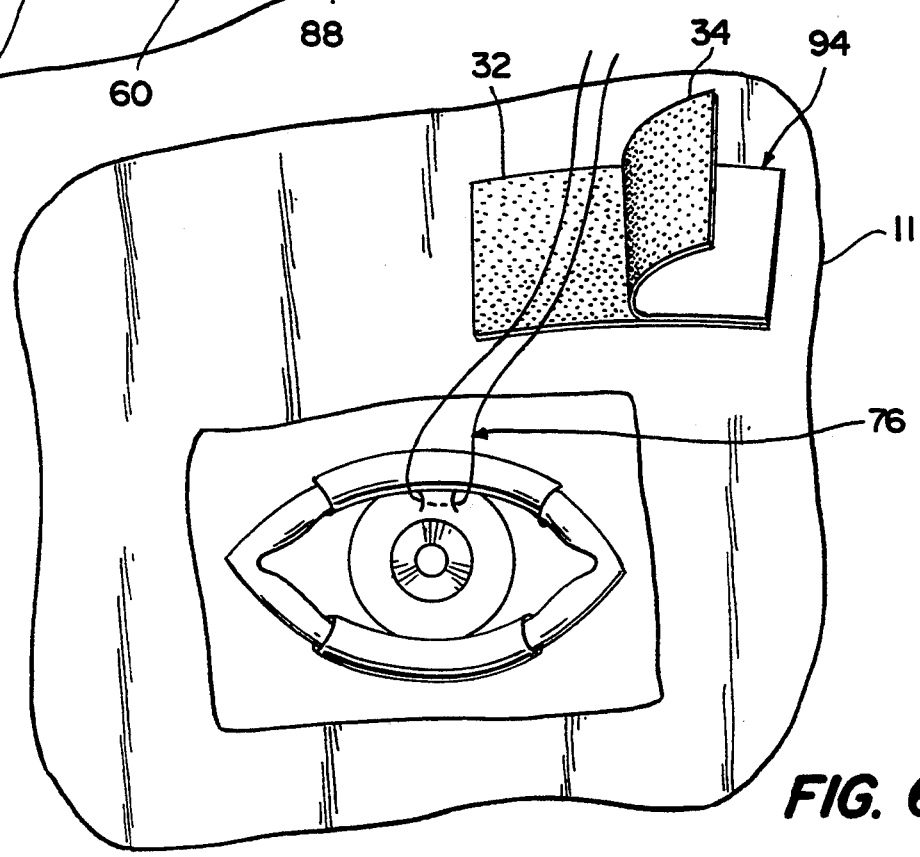
FIG. 6 is an enlarged, broken top view of another modification of a surgical drape having a superior rectus bridle suture fixator according to the present invention, the drape being shown in use covering the head of a patient.

A modification of a bridle suture fixator according to the present invention is shown in FIG. 6 at 94. The bridle suture fixator 94 is essentially the same as the bridle suture fixator 30 except that the bridle suture fixator 94 is attached directly to the surgical drape 11 and is provided without a head stabilizer. The bridle suture fixator 94 includes a fixation surface or layer 32 of activated adhesive disposed on the upper or proximal surface of the drape 11 and a cover sheet 34 disposed over the fixation surface 32. The fixation surface 32 can be provided on the drape 11 in many ways including depositing a layer of adhesive on the material of the drape and attaching a sheet carrying a layer of adhesive to the drape by sewing, stitching, adhesives and other various forms of bonding.

By stabilizing a patient's head relative to an operating table during cataract surgery, the present invention allows cataract surgery to be performed with greater precision, less difficulty and increased confidence while avoiding adverse complications and consequences of surgery. The present invention is particularly advantageous for cataract removal using phacoemulsification. By preventing lateral and forward movement of the patient's head during cataract surgery, the present invention ensures proper placement of surgical instruments utilized in cataract surgery while allowing the use of a local anesthetic. Additionally, the present invention allows a patient's head to be positioned on an operating table to optimize exposure of the eye while maintaining the optimal head position. By providing a head stabilizer as part of a surgical drape used to cover a patient's head during eye surgery, the present invention allows the head stabilizer to be positioned on a patient simultaneously with placement of the drape thusly simplifying surgical procedures of the eye and reducing the cost of and number of individual products associated with eye surgery. The superior rectus bridle suture fixator of the present invention enhances eye surgery by allowing superior rectus bridle sutures to be fixated with controlled, uniform tension and to be easily adjusted during eye surgery to vary the tension and fixation site of the bridle sutures to optimally position the eye. The bridle suture fixator allows superior rectus bridle sutures in either of the patient's eyes to be fixated with equal facility without obstructing the surgical field and without the need for clamps, tape and other extraneous devices. The cover of the bridal suture fixator, when disposed over the fixated ends of the suture, protects the fixated ends and inhibits inadvertent removal or displacement of the ends from a selected fixation site on the fixation surface. By providing a bridle suture fixator, with or without a head stabilizer, as part of a surgical drape used to cover a patient's head during eye surgery, the present invention allows the bridle suture fixator to be positioned over a patient's forehead simultaneously with placement of the drape thusly simplifying surgical procedures of the eye and reducing the cost of and number of separate products associated with eye surgery. The head stabilizer and bridle suture fixator device incorporated in surgical drapery is comfortable for the patient, easy to use under the time constraints of surgery, adaptable for use on diverse sizes of operating tables and is well suited for disposability, or single-patient use. When tightened, the head stabilizer and bridle suture fixator device includes the additional advantages of securing the drape in place, enhancing the sterility of the surgical field and improving access to the bridle suture fixator for adjusting eye position during surgery. The drainage device of the present invention allows a drain for draining excess fluid from the eye during eye surgery to be selectively, removably positioned and held in communication with the eye and a fluid collection bag to provide continuous drainage of fluids from the eye. By providing a drain holder, the present invention eliminates the need for surgical staff to continually position and manipulate drains at the eye during eye surgery. With the drain holder securing the drain in position relative to the eye, manipulation and movement of the drain at the eye is avoided such that the surgeon's field of view is not impaired. The wick of the present invention permits positioning of an end or part of the wick unobtrusively at the eye while be immovably held, via the drain holder, to enhance viewability of the operative site. Various types and sizes of wicks are compatible with the drain holder and fluid collection bag, and the drainage device can be integrated in a surgical drape allowing various components needed during eye surgery to be supplied as a single package thusly simplifying surgical procedures of the eye and reducing the costs of eye surgery as well as the number of separate items required in eye surgery.

Having described preferred and alternative embodiments of a new and improved head stabilizer and super rectus bridle suture fixator device and drainage device for use in eye surgery, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical drape and head stabilizer device for stabilizing a patient's head relative to an operating table supporting the patient's head during eye surgery including a sterile drape for being positioned over the patient's head;

an opening in said drape for exposing an eye of the patient to be operated;

a head stabilizer on said drape for being positioned, simultaneously with said drape, to extend across the forehead of the patient, said head stabilizer including a strap secured on said drape by stitching and having ends for being arranged in an overlapping configuration beneath the operating table; and fasteners on said ends for fastening said ends together in said overlapping configuration with the head stabilizer extending around the operating table laterally whereby the head of the patient is stabilized relative to the operating table.

2. A surgical drape and head stabilizer device as recited in claim 1 wherein said drape includes at least two layers of material and said strap is held between said layers of said drape.

3. A surgical drape and head stabilizer device as recited in claim 2 wherein said drape includes a sleeve and said strap is held within said sleeve.

4. A surgical drape and head stabilizer device as recited in claim 1 wherein said fasteners include complimentary hook and loop fabric strips on said ends.

5. A surgical drape and head stabilizer device as recited in claim 1 wherein said fasteners include adhesive surfaces on said ends.

6. A surgical drape and head stabilizer device as recited in claim 5 wherein said drape includes a pair of lateral sides and said ends protrude beyond said lateral sides.

7. A surgical drape and head stabilizer device as recited in claim 6 further including a pad on said drape to be disposed upon the patient's forehead when said drape is positioned over the patient's head.

8. A surgical drape and head stabilizer device as recited in claim 1 further including an adhesive fixation surface on said drape to be disposed adjacent the patient's forehead for fixating a superior rectus bridle suture with controlled tension.

9. A surgical drape and head stabilizer device as recited in claim 8 wherein said fixation surface is disposed on said head stabilizer.

10. A surgical drape and drainage device for draining fluid from the eye during eye surgery including a surgical drape for being positioned over the head of a patient undergoing eye surgery;

an opening in said drape for exposing an eye of the patient to be operated;

a fluid collection bag on said drape for collecting fluid drained from the eye;

a drain for communicating with the eye and said fluid collection bag for draining fluid from the eye; and a drain holder on said drape for securing said drain in communication with the eye and said fluid collection bag.

11. A surgical drape and drainage device as recited in claim 10 wherein said drain holder includes an adhesive attachment surface disposed on said drape and a cover sheet removably secured on said attachment surface.

12. A surgical drape and drainage device as recited in claim 11 wherein said drain includes a wick made of absorbable material and having ends for communicating, respectively, with the eye and said fluid collection bag.

13. A surgical drape and drainage device as recited in claim 12 wherein said fluid collection bag has an open upper end for receiving an end of said wick.

14. A surgical drape and drainage device as recited in claim 13 further including means on said upper end for sealing said fluid collection bag.

15. A surgical drape and drainage device as recited in claim 14 wherein said upper end of said fluid collection bag is disposed on said drape to be positioned at an elevation lower than the eye whereby fluid absorbed by said wick flows into said fluid collection bag by gravity.

16. A surgical drape and drainage device as recited in claim 15 wherein said wick includes an elongate, cylindrical body extending from the eye to said fluid collection bag.

17. A surgical drape and drainage device as recited in claim 15 wherein said wick includes a body having an elongate, cylindrical segment with an end to be disposed in said upper end of said fluid collection bag and a curved segment to be disposed at the fornix of the eye joined to said cylindrical segment at a junction allowing said cylindrical segment to be bent from said curved segment.

18. A surgical drape and drainage device as recited in claim 15 further including a head stabilizer on said drape for stabilizing the patient's head during eye surgery.

19. A surgical drape and drainage device as recited in claim 15 further including a fixation surface on said drape for fixating bridle sutures thereon with controlled tension.

20. A method of performing eye surgery on a patient including the steps of positioning a patient in a supine position on an operating table;

placing a surgical drape having a strap over the patient's head;

stabilizing the patient's head by positioning the strap of the drape around the patient's head and the operating table to prevent forward and lateral movements of the patient's head relative to the operating table; and performing a surgical procedure on an eye of the patient while the patient's head is stabilized.

21. A method of performing eye surgery on a patient including the steps of supporting the patient's head;

placing a surgical drape over the patient's head;

positioning a fixation surface on the drape upon the patient's forehead;

passing a bridle suture under the superior rectus of the patient's eye;

positioning the eye with the superior rectus bridle suture; and fixating the superior rectus bridle suture with controlled tension by contact with the fixation surface to maintain the position of the eye.

22. A method of performing eye surgery as recited in claim 21 further including, after said fixating step, the steps of releasing the superior rectus bridle suture from the fixation surface, adjusting the position of the eye with the superior rectus bridle suture and fixating the superior rectus bridle suture by contact with the fixation surface to maintain the adjusted position of the eye.

23. A method of performing eye surgery as recited in claim 22 further including the step of providing an adhesive fixation surface and a cover removably secured on the fixation surface and further including, prior to said fixating step, the step of removing the cover to expose at least a portion of the fixation surface.

24. A method of performing eye surgery as recited in claim 23 further including, after said fixating step, the step of replacing the cover on the fixation surface to further fixate the superior rectus bridle suture.

25. A method of performing eye surgery on a patient including the steps of supporting the patient's head;

placing a surgical drape over the patient's head with an opening exposing an eye of the patient to be operated;

positioning a fluid collection bag of the surgical drape at an elevation lower than the patient's eye;

positioning a drain in communication with the eye and the fluid collection bag;

securing the drain in communication with the eye and the fluid collection bag on a drain holder of the surgical drape; and performing a surgical procedure on the eye while draining excess fluids from the eye and into the fluid collection bag with the drain.

26. A method of performing eye surgery as recited in claim 25 wherein the drain holder includes an adhesive attachment surface and said step of securing includes securing the drain on the attachment surface.

27. A method of performing eye surgery as recited in claim 26 wherein the drain holder includes a cover removably secured on the attachment surface and further including, prior to said step of securing, the step of removing the cover to expose at least a portion of the attachment surface.

28. A method of performing eye surgery as recited in claim 27 further including, after said step of securing, the step of replacing the cover on the attachment surface.

29. A method of performing eye surgery as recited in claim 28 wherein said step of positioning the drain includes positioning the drain at the outer canthus of the eye.

30. A method of performing eye surgery as recited in claim 29 wherein said step of positioning the drain includes positioning the drain in the fornix of the eye.

31. A method of performing eye surgery as recited in claim 29 wherein the fluid collection bag includes an open end and said step of positioning the drain includes positioning an end of the drain in the open end of the fluid collection bag.

32. A method of performing eye surgery as recited in claim 31 further including, after said step of positioning the drain, the step of closing the open end of the fluid collection bag.

* * * * *